(12) United States Patent
Shippert

(10) Patent No.: US 6,530,125 B2
(45) Date of Patent: Mar. 11, 2003

(54) MULTI-PLANE GRIPPING HANDLE

(76) Inventor: Ronald D. Shippert, 4975 S. Albion St., Littleton, CO (US) 80121

(*) Notice: Subject to any disclaimer, the term of this patent is extended or adjusted under 35 U.S.C. 154(b) by 0 days.

(21) Appl. No.: 09/900,210

(22) Filed: Jul. 6, 2001

(65) Prior Publication Data

US 2003/0009854 A1 Jan. 16, 2003

(51) Int. Cl.⁷ .................................................. B25Q 1/10
(52) U.S. Cl. ..................... 16/430; 16/DIG. 12; 16/422; D8/107
(58) Field of Search ......................... 16/DIG. 12, 430, 16/431, 422; D8/107, 300, 83

(56) References Cited

U.S. PATENT DOCUMENTS

| | | | | |
|---|---|---|---|---|
| 1,162,896 A | * | 12/1915 | Achberger | 16/DIG. 12 |
| 1,217,287 A | * | 2/1917 | Dillinger | 16/DIG. 12 |
| 1,730,820 A | * | 10/1929 | Holden | 16/DIG. 12 |
| 2,520,355 A | * | 8/1950 | Bell | 16/DIG. 12 |
| D182,827 S | | 5/1958 | Latham | D22/3 |
| D193,496 S | | 8/1962 | Jacoff | D93/4 |
| D221,614 S | | 8/1971 | McMahon et al. | D8/94 |
| D230,468 S | | 2/1974 | Fairbairn | D8/107 |
| D245,062 S | | 7/1977 | Grame | D8/83 |
| D252,554 S | | 8/1979 | Lancer | D8/83 |
| D260,849 S | | 9/1981 | West et al. | D8/94 |
| 4,414,438 A | * | 11/1983 | Maier et al. | 200/6 A |
| 4,445,011 A | * | 4/1984 | Hansen | 200/52 R |
| 4,885,818 A | | 12/1989 | Arterbury | 16/110 R |
| 4,926,521 A | * | 5/1990 | Gagnepain | 16/DIG. 12 |
| 4,950,013 A | | 8/1990 | Yonkers | 294/49 |
| 5,299,497 A | * | 4/1994 | Dias | 16/DIG. 12 |
| D355,831 S | * | 2/1995 | Hull et al. | D8/107 |
| D357,947 S | * | 5/1995 | Richer | D21/48 |
| 5,440,784 A | * | 8/1995 | Hull et al. | 16/110 R |
| D373,944 S | | 9/1996 | Thompson et al. | D8/83 |
| D389,720 S | | 1/1998 | Warner et al. | D8/107 |
| D393,791 S | | 4/1998 | Halls et al. | D8/107 |
| 5,737,803 A | | 4/1998 | Tisdale | 16/111 R |
| 5,761,767 A | * | 6/1998 | Barton | 16/114 R |
| 5,802,960 A | | 9/1998 | Graj et al. | 99/403 |
| 5,805,256 A | * | 9/1998 | Miller | 348/734 |
| D399,722 S | * | 10/1998 | Eidsmore et al. | D8/107 |
| D403,228 S | | 12/1998 | Halls et al. | D8/107 |
| D403,946 S | * | 1/1999 | Shih | D8/303 |
| D404,280 S | * | 1/1999 | Wen | D8/107 |
| D425,365 S | * | 5/2000 | Chien | D8/107 |
| 6,065,188 A | * | 5/2000 | Wold et al. | 16/430 |
| D426,135 S | * | 6/2000 | Lee | D8/107 |
| D426,136 S | * | 6/2000 | Yu | D8/107 |
| D427,030 S | * | 6/2000 | Wen | D8/1 |
| D454,048 S | * | 3/2002 | Lin | D8/107 |

* cited by examiner

*Primary Examiner*—Thomas B. Will
*Assistant Examiner*—Alexandra K Pechhold
(74) *Attorney, Agent, or Firm*—Sheridan Ross P.C.

(57) ABSTRACT

A multi-plane gripping handle for use with a multitude of devices is provided which generally comprises a handle section, a thumb section and a butt surface. The size and shape of the handle section and thumb section are selected to optimize the surface contact between the gripping handle and the hand of the user. The handle section and the thumb section each occupy a separate plane and these in planes are arranged in a selected angular relationship with one another to further optimize the gripping surface contact between the hand and the handle. In an alternative embodiment, the gripping handle may be formed in a split-case construction such that alternative devices may be interchangeably inserted into the gripping handle and thus allow for the gripping handle to be used with various devices.

23 Claims, 7 Drawing Sheets

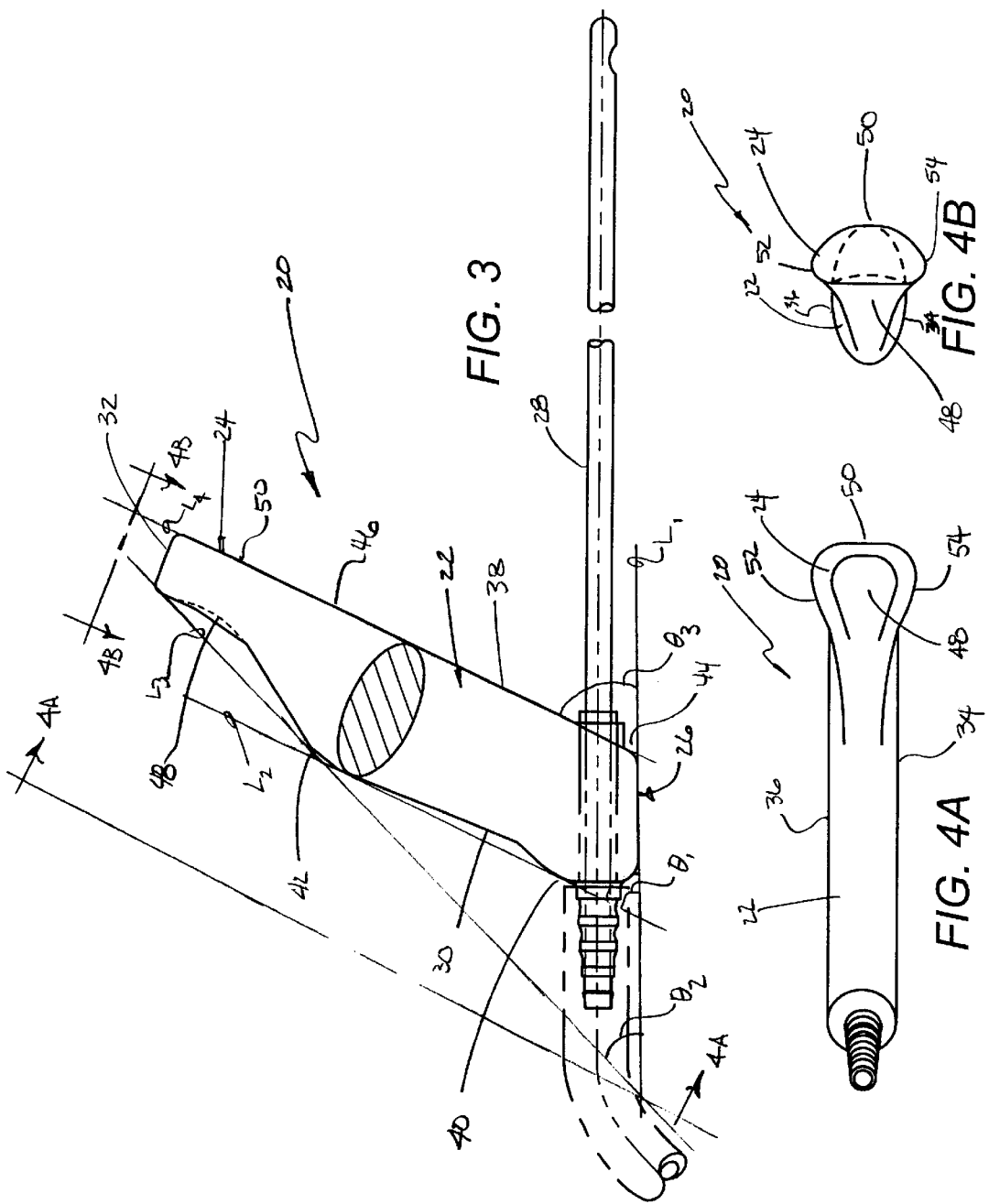

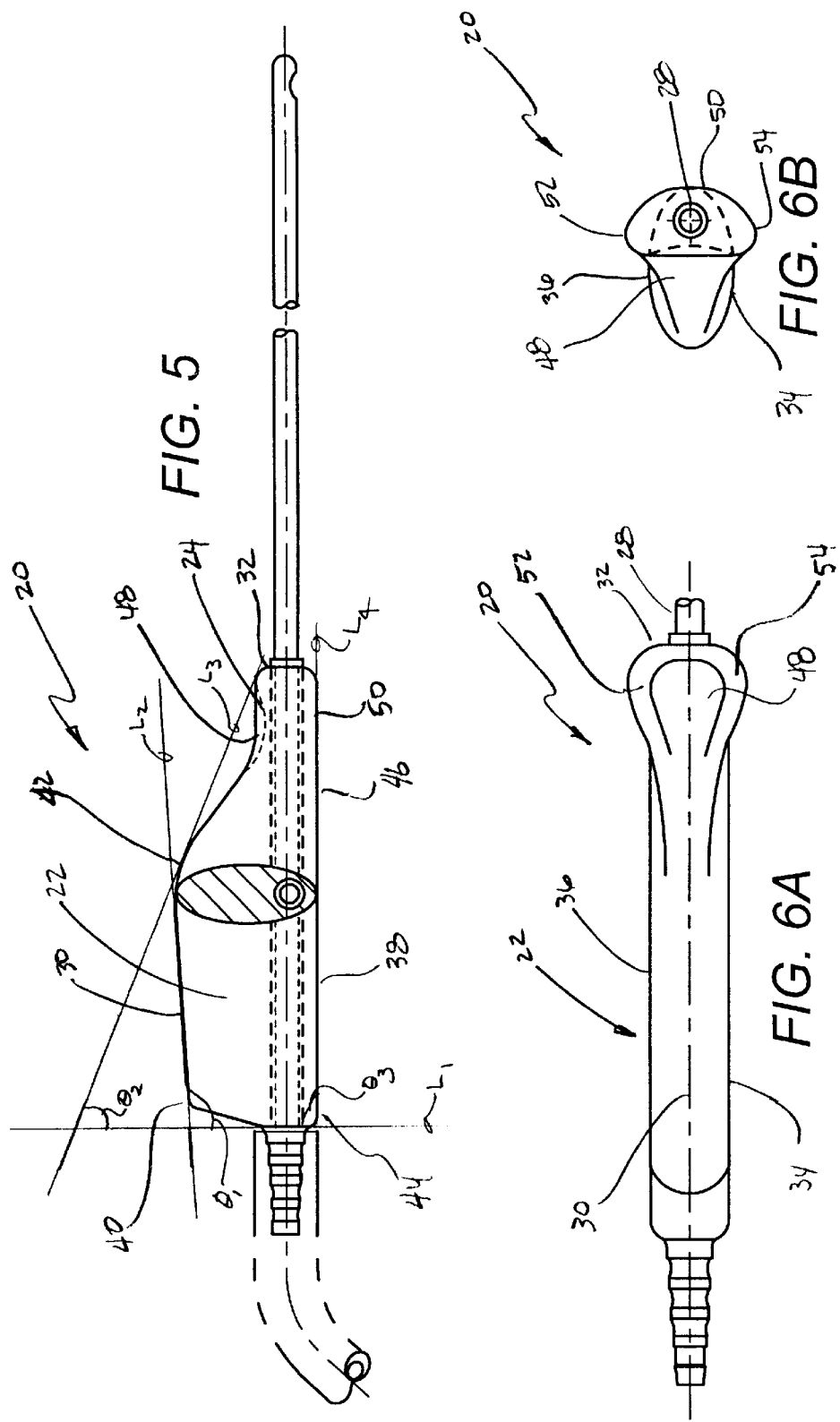

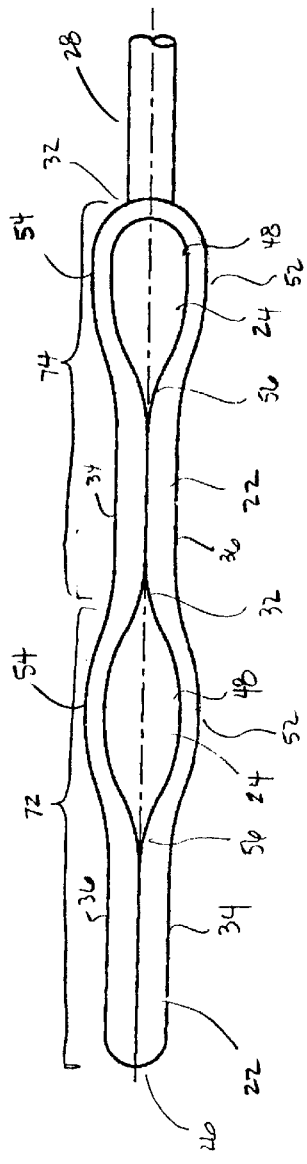
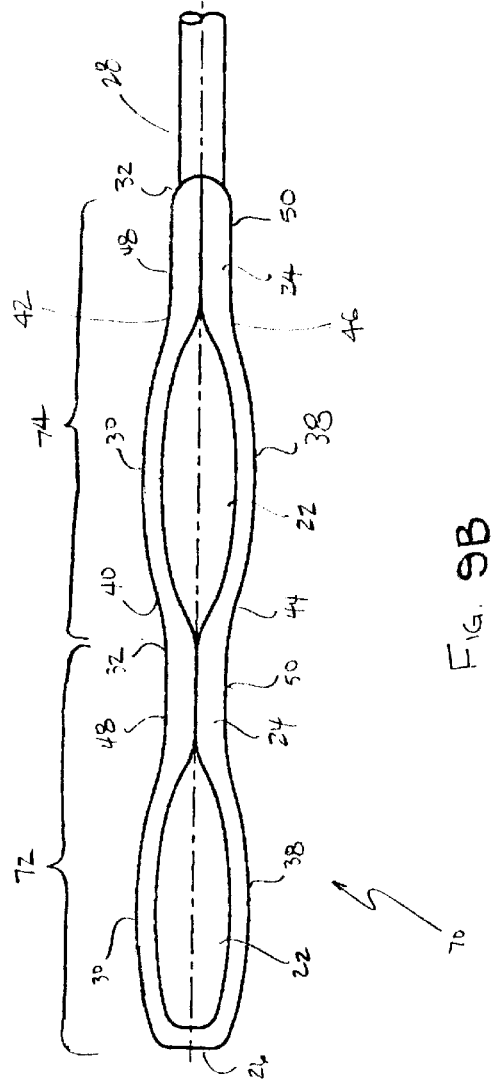
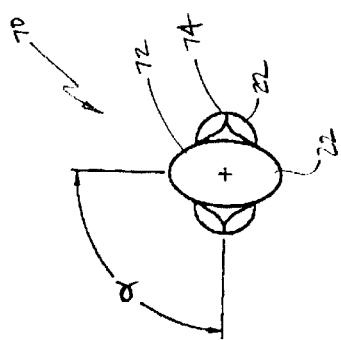

MULTI-PLANE GRIPPING HANDLE

FIELD OF THE INVENTION

The present invention relates to gripping handles that can be part of tools, medical instruments and other devices and more particularly to multi-plane gripping handles having two anatomically shaped surface planes adapted for use with such devices.

BACKGROUND OF THE INVENTION

Various types of gripping handles are currently available for use with numerous devices. These handles are intended to provide a surface with which a user may grasp the device for manipulation, such as transportation or implementation, of the device to perform its intended function.

Commonly, present gripping handles take the form of a round, rectangular, hexagonal, or other regular geometric shape in a single plane along the axis of a shaft of the attached device. Unfortunately, these types of handles do not fit the human hand well, and thus a limited surface area of the hand contacts the handle. Additionally, these shapes create a poor friction surface between the handle and the user's hand. The limited surface contact and poor friction surface of these handles have minimal torque capacity. A user is required to exert a great amount of strength, surface friction, and leverage to adequately perform a given task with these handles. In some cases, these disadvantages may create a need for longer lever arms or added elements, such as abrasives or a textured surface, or may increase necessary rest periods during operation. Also, for more complex devices and associated tasks, users of the present handles may require additional training and practice to efficiently utilize a given device for an associated task.

An additional problem with present gripping handles is the permanent interconnection of the handle to the attendant device. In certain situations, an interchangeable gripping handle for use with various devices would provide a cost benefit. In an example from the medical field, a surgeon may require several cannula handle units to perform a liposuction case. Cannulas of various sizes may be desirable to perform work on various portions of the patient. Cannulas, especially smaller bore cannulas, may be difficult, if not impossible, to properly sterilize for reuse. Cannulas which cannot be properly sterilized must be discarded for hygienic reasons. If a permanent gripping handle is provided with each individual cannula, the gripping handle must necessarily be discarded as well. The use of individual cannulas with permanent gripping handles attached becomes expensive. The initial cost of cannulas is greater because of the more complex part. It is also expensive to maintain, e.g., sterilize, repair, or replace, the cannulas.

In view of the foregoing perceived deficiencies, it would be advantageous to provide a gripping handle which includes at least two anatomically-shaped gripping surface planes, wherein each plane has a specified length, width, and thickness and wherein a selected angular relationship exists between the planes. It would be further advantageous to provide a gripping handle wherein the surface planes, lengths, widths, and thicknesses correspond with the normal gripping posture of the average human hand, thereby optimizing the surface contact between the user's hand and the handle. It would also be advantageous to provide a gripping handle which may be used interchangeable with various devices.

SUMMARY OF THE INVENTION

The multi-plane gripping handle of the present invention generally includes a handle section, a thumb section, and a butt surface. The handle section of the present invention includes a palm sidewall, a finger sidewall, an outer surface, and an inner surface. The outer surface has an outer end and an outer common end, and the inner surface has an inner end and an inner common end. The thumb section includes a thumb upper wall, a lower wall, first and second sidewalls, a distal end and an opposite end.

The normal human hand grip occurs in two separate planes, that when combined produce one curvilinear plane. The planes consist of a finger to thumb (FT) plane and a finger to palm (FP) plane. The FT plane, in an normal gripping posture, is created between the index finger and the thumb. The FP plane, in a similar posture, is created between the fingers and the palm of the hand. The dimensions of the handle section, and its individual elements, of the present invention are selected to optimize the contact surface area between the gripping handle and the FP plane. Similarly, the dimensions of the thumb section are selected to optimize the contact surface area between the handle and the FT plane. By fitting the hand in this manner, several advantages are provided. The gripping handle of the present invention requires less strength to grip and provides greater torque transfer due to increased leverage. The gripping handle thereby reduces fatigue and joint stress to the user. Additionally, a user of the gripping handle is able to manipulate the associated device with better accuracy and control.

The multi-plane gripping handle of the present invention is further defined by the angular relationships between the certain elements of the handle. A first angle is determined by the intersection of a line extending through the butt surface and a line extending through the outer surface of the handle section. A second angle is determined by the intersection of a line extending through the butt surface, as in the first angle, and a line extend from the outer common end of the handle section through the distal end of said thumb section. Typically, the first angle is less than 90° and the second angle is in the range of 35° and 55°.

The FT and FP planes described above each have a separate specific gripping strength when occurring separately. However, when the two planes occur together at a proper angular relationship, there is a trapping effect between the hand and the gripping handle. The trapping effect provides a greater torque transfer to the gripping handle of the present invention than achievable by bi-planar gripping alone. As described above, the increase of torque transfer to the handle creates less fatigue and joint stress in the user and requires less strength to perform a similar operation than a gripping handle of the prior art.

BRIEF DESCRIPTION OF THE DRAWINGS

FIG. 3 is a side elevation view of the handle of FIG. 1;

FIG. 4A is a plan view of the handle embodied in FIG. 3 along a plane parallel to the outer surface of the handle;

FIG. 4B is an end view from the distal end of the handle of FIG. 3;

FIG. 5 is a side elevation view of the handle of FIG. 2;

FIG. 6A is a top plan view of the handle of FIG. 5;

FIG. 6B is an end view of the handle of FIG. 5;

FIG. 9A is a top plan view of an embodiment of a two hand gripping handle of the present invention;

FIG. 9B is a side elevation view of the two hand gripping handle of FIG. 9A; and FIG. 9C is an end view of the two hand gripping handle of FIG. 9A.

DETAILED DESCRIPTION

Figure 1:
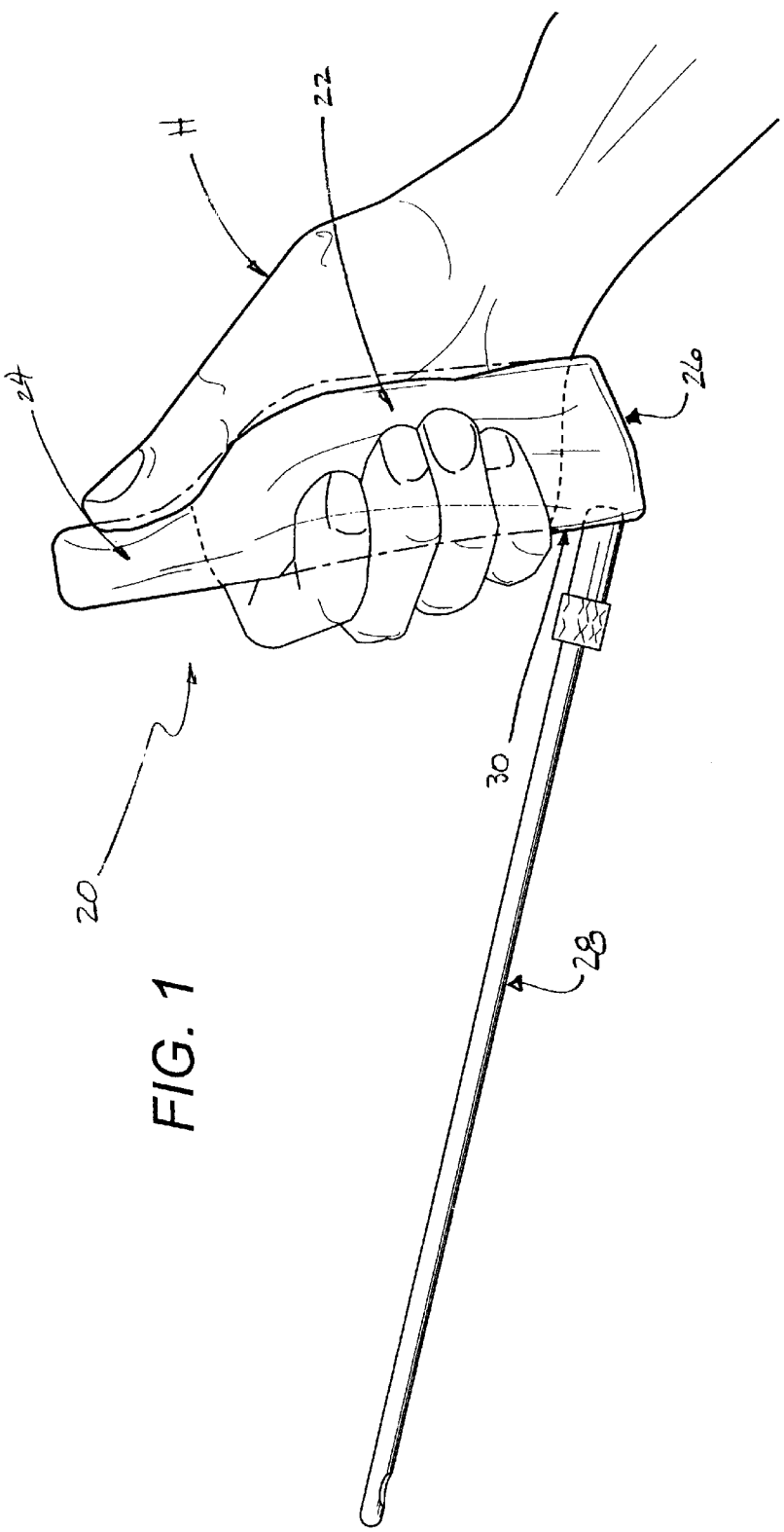
FIG. 1 is a side elevation view of one embodiment of a handle of the present invention shown gripped by a human hand.
Figure 2:
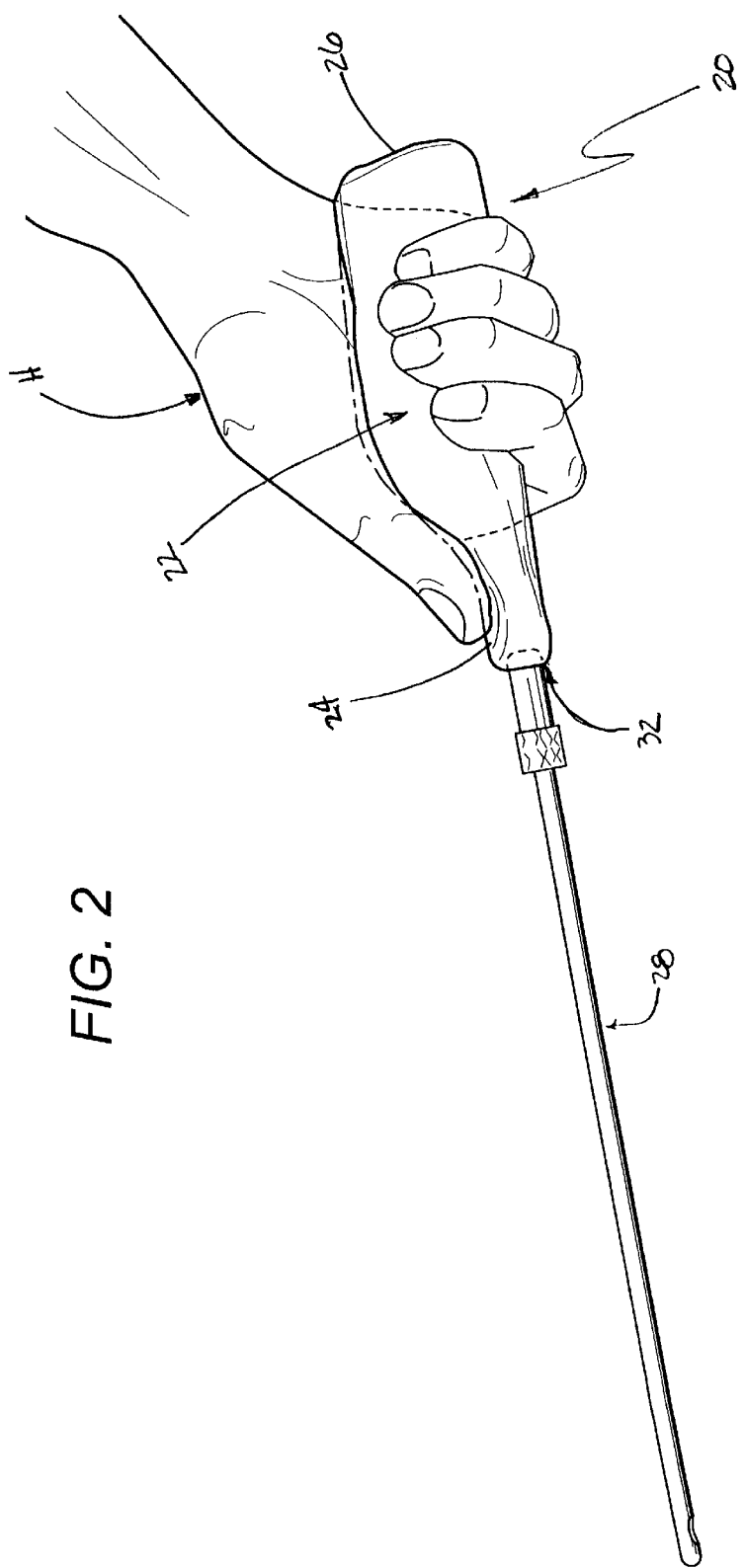
FIG. 2 is a side elevation view of another embodiment of a handle of the present invention shown gripped by a human hand.

With reference to FIGS. 1 and 2, two embodiments of a multi-plane gripping handle 20 of the present invention is illustrated as gripped by a human hand H. In each embodiment the multi-plane gripping handle 20 generally comprises a handle section 22, a thumb section 24 joined to the handle section 22, and a butt surface 26 adjacent to the handle section 22 opposite the thumb section 24. The handle section 22 and the thumb section 24, although joined together, are separate segments defining a gripping plane for the human hand. The handle section 22 creates a gripping surface in a finger-palm (FP) plane segment, i.e., the segment between the fingers and the palm of the users hand. The thumb section 24 creates a gripping surface in a finger-thumb (FT) plane segment, i.e., the segment between the index finger and the thumb of the users hand. The orientation of these planes is designed to fit a common grip of the normal human hand thereby increasing the surface contact between a user's hand and the gripping handle 20. The individual elements of the handle section 22 and the thumb section 24 creating these planes is discussed in more detail below.

In FIG. 1, the multi-plane gripping handle 20 is shown in an embodiment with the device 28, in this case a liposuction cannula, interconnected to the outer surface 30 of the handle section 22 near the butt section 26. The handle 20, in this orientation, forms an L-style handle, i.e., the device 28 forms an L-shape with the handle 20.

In FIG. 2, the multi-plane gripping handle 20 of the present invention is shown in a more traditional embodiment wherein the device 28 extends axially from the gripping handle 20. In this embodiment, the device 28 is interconnected with a distal end 32 of the thumb section 24.

With reference to FIGS. 3, 4A, and 4B, the embodiment of the multi-plane gripping handle 20 of FIG. 1 is shown in various views. FIG. 3 shows the handle 20 of FIG. 1 in side elevation view. FIG. 4A shows this embodiment of the handle in plan view as viewed from line "4A—4A". Similarly, FIG. 4B shows this embodiment in plan view as viewed along line "4B—4B." In this embodiment, the device 28 extends through the handle 20 adjacent to, and substantially parallel with, the butt surface 26. The handle section 22 generally comprises a palm sidewall 34, a finger sidewall 36, an outer surface 30, and an inner surface 38 to create a gripping surface in a finger-palm (FP) plane segment, i.e., the segment between the fingers and the palm of the users hand. The cross-sectional area of the handle section 22 is generally ovate as depicted by the crosshatched area of FIG. 3. The palm sidewall 34 and finger sidewall 36 typically are arranged along the major axis of the ovate area, and the outer surface 30 and the inner surface 38 are arranged along the minor axis. However, the generally ovate area may be varied to some degree such that the palm sidewall 34 and the finger sidewall 36 are substantially flat. The outer surface 30 of the handle section 22 includes an outer end 40 and an outer common end 42. The inner surface 38 of the handle section 22 includes an inner end 44 and an inner common end 46. The outer common end 42 and the inner common end 46 are adjacent to the thumb section 24.

The thumb section 24 generally comprises a thumb upper wall 48, a lower wall 50, a first sidewall 52 and a second sidewall 54 to create a gripping surface in a finger-thumb (FT) plane segment, i.e., the segment between the index finger and the thumb of the users hand. The thumb section 24 also includes a distal end 32 and an opposite end. The opposite end is adjacent to the outer common end 42 and the inner common end 46 of the handle section 22.

The butt surface 26 is a surface extending from the outer end 40 of the handle section outer surface 30 and the inner end 44 of the handle section inner surface 38.

With reference to FIGS. 5, 6A, and 6B, the embodiment of the multi-plane gripping handle 20 of FIG. 2 is shown in various views. FIG. 5 shows the handle 20 of FIG. 2 in side elevation view. FIG. 6A shows this embodiment of the handle 20 in top plan view and FIG. 6B shows this embodiment in end elevation view as viewed from the device 28 end. In this embodiment, the device 28 extends through the handle 20 from the distal end 32 of the thumb section 24 to the butt surface 26 (FIG. 2) substantially parallel with the inner surface 38 of the handle section 22. As described above, the handle section 22 generally comprises a palm sidewall 34, a finger sidewall 36, an outer surface 30, and an inner surface 38 to create a gripping surface in a finger-palm (FP) plane segment, i.e., the segment between the fingers and the palm of the users hand. The cross-sectional area of the handle section 22 is generally ovate as depicted by the crosshatched area of FIG. 5. The palm sidewall 34 and finger sidewall 36 typically are arranged along the major axis of the ovate area, and the outer surface 30 and the inner surface 38 are arranged along the minor axis. As above, the generally ovate area may be varied to some degree such that the palm sidewall 34 and the finger sidewall 36 are substantially flat. The outer surface 30 of the handle section 22 includes an outer end 40 and an outer common end 42, and the inner surface 38 of the handle section 22 includes an inner end 44 and an inner common end 46. The common ends 42 and 46 are adjacent to the thumb section 24.

As above, the thumb section 24 generally comprises a thumb upper wall 48, a lower wall 50, a first sidewall 52 and a second sidewall 54 to create a gripping surface in a finger-thumb (FT) plane segment, i.e., the segment between the index finger and the thumb of the user's hand. The thumb section also includes a distal end 32 and an opposite end 56 adjacent to the handle section 22. The butt surface 26 extends from the outer end 40 of the handle section outer surface 30 and the inner end 44 of the handle section inner surface 38.

Referring again to FIGS. 3 and 5, the multi-plane gripping handle 20 of the present invention is defined by the angular relationships between the various surfaces of the handle 20. A first angle $\theta_1$ can be defined as being formed at the intersection of a first line $L_1$ extending generally along the butt surface 26 (a line fitted to the butt surface 26 and preferably no part of the line being located inwardly of the butt surface 26) and a second line $L_2$ extending generally through the outer surface 30 of the handle section 22 (a line fitted to the outer surface 30 and preferably no part of the line being located inwardly of the outer surface 30). In order to optimize the fit of the handle 20 to a user's hand, the first angle $\theta_1$ is typically less than 90°. A second angle $\theta_2$ can be defined as being formed at the inner section of the first line $L_1$ and a third line $L_3$ extending generally from the outer common end 42 of the handle section 22 through the distal end 32 of the thumb section 24 (a line fitted thereto and preferably no part of the line is located inwardly of the outer common end 42 and the distal end 32). Second angle is typically in the range of 35°–55°. Additionally, the first angle $\theta_1$ is typically greater than the second angle $\theta_2$.

The relationship of the various surfaces may also be defined in an alternative embodiment by a third angle $\theta_3$. The third angle $\theta_3$ is formed between the first line $L_1$ and a fourth line $L_4$ extending generally along the lower wall 50 of the thumb section 24 (a line fitted to the lower wall 50 and preferably no part of the line being located inwardly of the lower wall 50). In this embodiment, the third angle $\theta_3$ is typically greater than the second angle $\theta_2$, and the third angle $\theta_3$ is closer in magnitude to the first angle $\theta_1$ than it is to the second angle $\theta_2$.

In each of the above embodiments, the dimensions of the handle section 22 and the thumb section 24 may be selected to optimize the fit between a user's hand and the gripping handle 20. Typically, the length of the handle section 22 is at least twice the length of the thumb section 24. More typically, the length of the handle section 22 is in the range of 3.5 to 5.5 inches, and the length of the thumb section 24 is in the range of 1.5 to 2.5 inches.

The widths and thickness of the handle section 22 and the thumb section 24 may also be selected to optimize surface contact between a user's hand and the gripping handle 20. Typically, the handle section is designed with a width in the range of 1.0 to 1.75 inches and a thickness in the range of 0.6 to 1.0 inch. The thumb section typically has a width in the range of 1.0 to 1.75 inches and a thickness in the range of 0.6 to 1.0 inch.

In one specific embodiment designed to fit most human hands, the length of the handle section 22 is about 4.75 inches and the length of the thumb section is about 2 inches. In this embodiment, the width of the handle section 22 is about 1.75 inches, the width of the thumb section 24 is about 1.4 inches and the thicknesses of each section is about 0.8 inch.

Based on the foregoing design constraints, the gripping handle 20 of the present invention may provide up to 33.5 square inches of possible surface area for contact with a user's hand. Most prior art gripping handles provide only about 16 square inches of possible surface area for user contact. In general, and assuming an ergonomic fit between the hand and the gripping handle, there is a direct relationship between the amount of surface of the hand in contact with the gripping handle and the control, grip, and mechanical advantage of the handle and the associated device. The available surface area for contact of the average human hand, palmar surface only, is approximately 26 square inches for the adult male (plus/minus 25%) and 21 square inches for an adult female (plus/minus 25%). Therefore, the gripping handle 20 of the present invention provides an available gripping surface area which may utilize most of the available surface of the human hand.

The increased surface area of contact between a user's hand and the gripping handle 20 provides several advantages. For example, the present gripping handle 20 may allow a torque transfer from the user on the order of 62.5 inch-pounds. In contrast, a linear octagonal handle of the prior art allows torque transfer of approximately 43 inch-pounds. A user operating a linear rectangular handle will only produce about 30 inch-pounds. The increased ability to transfer torque decreases user fatigue and strain on joints and muscles. Correspondingly, there present gripping handle 20 provides a user with greater control and precision of the attached device 28.

Figures 7A, 7B:
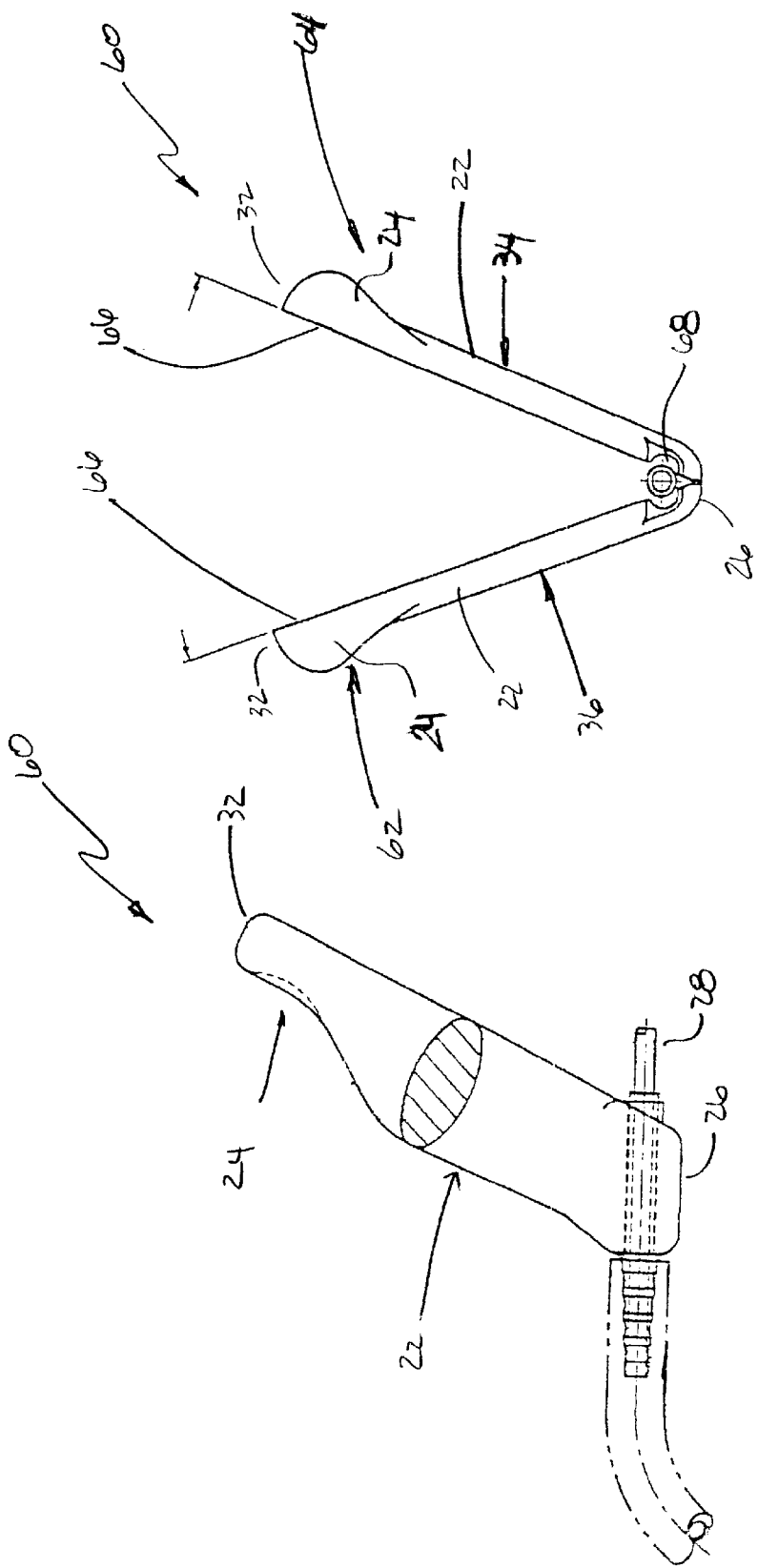
FIG. 7A is side elevation view of an alternative embodiment of the gripping handle of the present invention.
FIG. 7B is an end elevation view of the gripping handle of FIG. 7A.

With reference to FIGS. 7A and 7B, an additional embodiment of the split-case gripping handle 60 of the L-style construction of the present invention is shown. The split-case gripping handle 60 of this embodiment has the elements of the gripping handle 20 shown in FIGS. 3, 4A, and 4B, however the split-case handle 60 is constructed of a left handle portion 62 and a right handle portion 64 with common mating surfaces 66. In the embodiment of FIGS. 7A and 7B, the common mating surfaces 66 of the left handle portion 62 and the right handle portion 64 extend from the distal end 32 of the thumb section 24 to the butt surface 26. The left handle portion 62 and the right handle portion 64 are hingedly interconnected along the butt surface 26. A device aperture 68 is provided adjacent to the common mating surfaces 66 for insertion of a device 28.

Figure 8B:
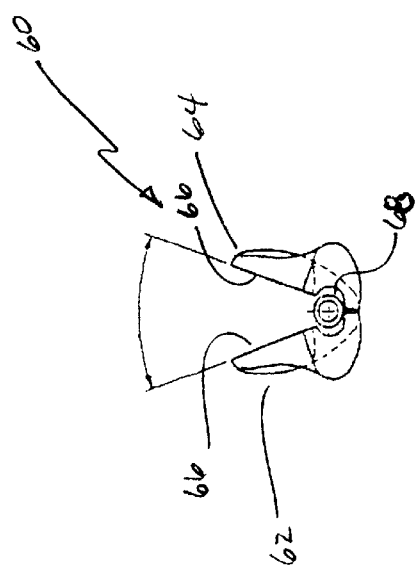
FIG. 8B is a side elevation view of the gripping handle of FIG. 8A.
Figure 8A:
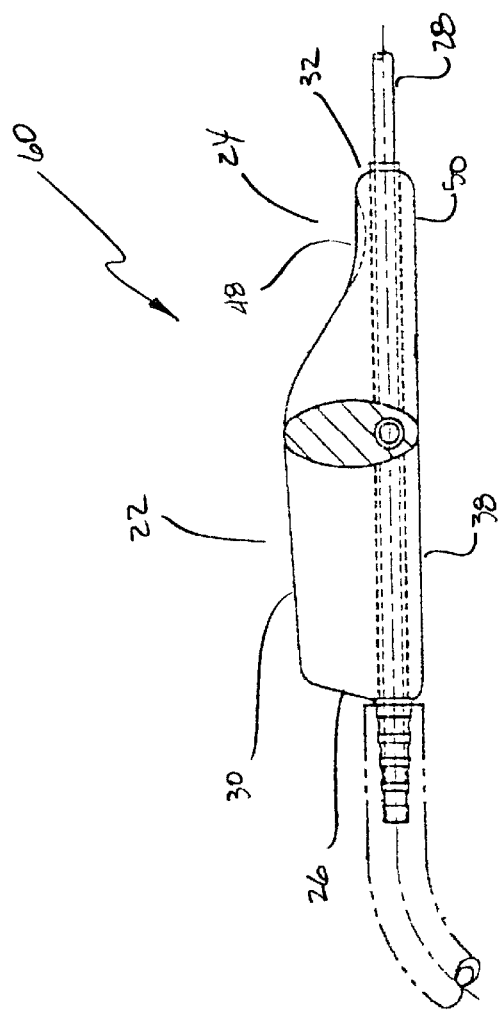
FIG. 8A is a side elevation view of another alternative embodiment of the gripping handle of the present invention.

With reference to FIGS. 8A and 8B, a similar additional embodiment of a split-case handle 60 is provided. The split-case handle 60 of this embodiment is a variation on the gripping handle 20 shown in FIGS. 5, 6A, and 6B. As in the L-style construction, the split-case handle has a left handle portion 62 and a right handle portion 64 with common mating surfaces 66. However, in this embodiment the common mating surfaces 66 extend, over the length of the split-case handle 60, from the outer surface 30 of the handle section 22 and the thumb upper wall 48 to the inner surface 38 of the handle section 22 and the lower wall 50 of the thumb section 24. The left handle portion 62 and the right handle portion 64 are hingedly interconnected along the inner surface 38 of the handle section 22 and the lower wall 50 of the thumb section 24. Again, a device aperture 68 is provided adjacent to the common mating surfaces 66 for insertion of a device 28.

The various embodiments of the split-case handle 60 may be used in tandem to allow a user to use alternative handle arrangements with a single device 28. For example, a surgeon performing a liposuction case may opt to use the split-case handle 60 embodiment shown in FIGS. 8A and 8B with a selected cannula for a portion of the surgery and later use the same cannula with the split-case handle 60 embodiment of FIGS. 7A and 7B. Additionally, a single split-case handle 60 may be used with various devices 28. For example, a surgeon my elect to interchange cannulas of various sizes and geometries during a liposuction case with the same split case handle 60. In this example, small bore cannulas which are difficult to sterilize may be discarded after the surgery while the handles 60 may be sterilized for reuse. Since only the cannulas need to be discarded, a cost savings in handle costs is achieved.

Referring now to FIGS. 9A, 9B, and 9C, yet another alternative embodiment of the gripping handle of the present invention, a two-hand gripping handle 70, is shown in top plan view, side elevation view and end elevation view, respectively. A two-hand gripping handle 70 incorporates two individual gripping handles 20 as described above for use with a device. In this way a tool or other device that requires the use of both hands of a user may be provided with a handle that reduces muscular fatigue, joint stress, and provides increased torque transfer and other advantages as listed above. In the embodiment shown, the two-hand gripping handle 70 has a first hand portion 72 and a second hand portion 74. Both the first hand portion 72 and the second hand portion 74 of the two-hand handle 70 generally comprise a handle section 22 and a thumb section 24. The handle section 22 generally comprises a palm sidewall 34, a finger sidewall 36, an outer surface 30, and an inner surface 38 to create a gripping surface in a finger-palm (FP) plane segment, i.e., the segment between the fingers and the palm of the users hand. The cross-sectional area of the handle section 22 is generally ovate as depicted by the crosshatched area of FIG. 3. The palm sidewall 34 and finger sidewall 36 typically are arranged along the major axis of the ovate area, and the outer surface 30 and the inner surface 38 are arranged along the minor axis. However, the generally ovate area may be varied to some degree such that the palm sidewall 34 and the finger sidewall 36 are substantially flat. The outer surface 30 of the handle section 22 includes an outer end 40 and an outer common end 42. The inner surface 38 of the handle section 22 includes an inner end 44 and an inner common end 46. The outer common end 42 and the inner common end 46 are adjacent to the start of the thumb section 24.

The thumb section 24 generally comprises a thumb upper wall 48, a lower wall 50, a first sidewall 52 and a second sidewall 54 to create a gripping surface in a finger-thumb (FT) plane segment, i.e., the segment between the index finger and the thumb of the users hand. The thumb section 24 also includes a distal end 32 and an opposite end 56. The opposite end 56 is adjacent to the outer common end 42 and the inner common end 46 of the handle section 22.

In the embodiment of FIGS. 9A, 9B, and 9C, the first hand portion 72 further comprises a butt surface 26. The butt surface 26 is a surface extending from the outer end 40 of the handle section outer surface 30 and the inner end 44 of the handle section inner surface 38.

With further reference to FIGS. 9A, 9B, and 9C, the first hand portion 72 is substantially axially aligned with the second hand portion 74. The thumb section distal end 32 of the first hand portion 72 is adjacently interconnected to the outer end 40 and inner end 44 of the handle section 22 of the second hand portion 74. It is understood, however, that other embodiments are included in the present invention. For example, a spacing element (not shown) may be provided between the first hand portion 72 and the second hand portion 74 to allow proper ergonomic spacing or leverage between the user's hands based upon the tool or device 28, e.g., a shovel.

With particular reference to FIG. 9C, the two-hand gripping handle 70 may be further defined by the angular relationship between the first hand portion 72 and the second hand portion 74. For clarity, the angular relationship is referenced from common elements of both the first hand portion 72 and the second hand portion 74. In FIG. 9C, the angular relationship, denoted by angle α, is measured from the handle section outer surface 30 of each the first handle portion 72 and the second handle portion 74. The angular relationship, i.e., the magnitude of angle α, is typically in the range of 0° to 90°, and preferably about 45°. The angular relationship, i.e., angle α, may be fixed at manufacturing. However, it is possible that the angular relationship may be adjustable in certain embodiments of the two-hand gripping handle 70. The adjustability can be accomplished by conventional means, such as by friction fit, luer lock, or a ratchet-like mechanism.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiments described herein above are further intended to explain the best mode presently known of practicing the invention, and to enable others skilled in the art to utilize the invention as such, or in other embodiments, and with various modifications required by their particular application or uses of the invention. It is intended that the appended claims be construed to include alternative embodiments to the extent permitted by the prior art.

To assist in the understanding of the invention and associated drawings, the following list of components and associated numbering are included herein:

| # | Component |
|---|---|
| 20 | multi-plane gripping handle |
| 22 | handle section |
| 24 | thumb section |
| 26 | butt surface |
| 28 | device |
| 30 | handle section outer surface |
| 32 | thumb section distal end |
| 34 | palm sidewall |
| 36 | finger sidewall |
| 38 | handle section inner surface |
| 40 | handle section outer end |
| 42 | handle section outer common end |
| 44 | handle section inner end |
| 46 | handle section inner common end |
| 48 | thumb upper wall |
| 50 | thumb section lower wall |
| 52 | first sidewall |
| 54 | second sidewall |
| 56 | thumb section opposite end |
| 60 | split-case handle |
| 62 | left handle portion |
| 64 | right handle portion |
| 66 | mating surface |
| 68 | device aperture |
| 70 | two-band gripping handle |
| 72 | first handle portion |
| 74 | second handle portion |

What is claimed is:

1. A handle in combination with a working device, comprising:

a handle section for contact with the palm and fingers of a user including a palm sidewall, a finger sidewall, an outer surface and an inner surface and a butt surface at a bottom of said handle section, said outer surface having an outer end and an outer common end, said inner surface having an inner end and a common inner end, said handle section having a cross-section that is substantially ovate, each of said palm sidewall and said finger sidewall being substantially flat;

a thumb section for contact with the thumb of the user joined to said handle section, said thumb section including a thumb upper wall, a lower wall, a first sidewall and a second sidewall, said thumb section with a distal end and an opposite end joined to said handle section, said thumb section having a front portion with a first length and a back portion with a second length that intersects said front portion to define an angle, said second length being greater than one-half of said first length and said back portion terminating adjacent to said common outer end and said common inner end;

a butt surface extending between said outer end of said handle section outer surface and said inner end of said handle section inner surface; and a working device held in said handle section and extending in a direction that is different from perpendicular to said butt surface;
wherein a first angle is defined between a line extending through said butt surface and a line extending through said handle section outer surface, a second angle is defined between a line extending through said butt surface and a line extending from said outer common end of said handle section through said distal end of said thumb section, said first angle being different from 90°, said first angle being greater than said second angle, and said second angle being in the range of 35°–55°.

2. A handle in combination with a working device, as claimed in claim 1, wherein:
said finger sidewall has a number of widths extending between said outer and inner surfaces of said handle section.

3. A handle in combination with a working device, as claimed in claim 1, wherein:
a third angle is defined between a line extending along said lower wall of said thumb section and a line extending along said butt surface, said line extending along said lower wall not extending inwardly of said thumb section, said third angle being greater than said second angle and in which said third angle is closer in magnitude to said first angle than to said second angle.

4. A handle in combination with a working device, as claimed in claim 1, wherein:
said first angle is in the range of 65°–85°.

5. A handle, as claimed in claim 1, wherein:
said second angle is about 45°.

6. A handle in combination with a working device, as claimed in claim 1, wherein:
each of said handle section and said thumb section has a length, said length of said handle section being in the range of 3.5–5.5 inches and said length of said thumb section being in the range of 1.5–2.5 inches.

7. A handle in combination with a working device, as claimed in claim 1, wherein:
each of said handle section and said thumb section has a width, said width of said handle section being in the range of 1.0–1.75 inches and said width of said thumb section being in the range of 1.0–1.75 inches.

8. A handle in combination with a working device, as claimed in claim 1, wherein:
each of said handle section and said thumb section has a thickness, said thickness of said handle section being in the range of 0.6–1.0 inch and said thickness of said thumb section being in the range of 0.6–1.0 inch.

9. A handle in combination with a working device, as claimed in claim 1, wherein:
said working device includes a cannula connected substantially parallel to said butt surface.

10. A handle in combination with a working device, as claimed in claim 1, wherein:
said thumb section has a width and said handle section has a thickness and in which said width of said thumb section is substantially the same as said thickness of said handle section.

11. A handle in combination with a working device, as claimed in claim 1, further comprising:
a left handle portion having a first mating surface and a first device recess; and
a right handle portion having a second mating surface and a second device recess;
wherein said first and second mating surfaces may be positioned adjacent to one another to form the handle with a device aperture.

12. A handle in combination with a working device, as claimed in claim 11, wherein:
said left handle portion and said right handle portion are hingedly interconnected.

13. A handle in combination with a working device, as claimed in claim 11, wherein:
said mating surfaces extend from said distal end of said thumb section to said butt surface.

14. A handle in combination with a working device, as claimed in claim 11, wherein:
said mating surfaces extend from said outer surface of said handle section and said thumb wall to said inner surface of said handle section and said lower wall of said thumb section.

15. A handle comprising:
a handle section for contact with the palm and fingers of a user including a palm sidewall, a finger sidewall, an outer surface and an inner surface, said outer surface having an outer end and a common outer end, said inner surface having an inner end and a common inner end, said handle section having a cross-section that is substantially ovate, each of said palm sidewall and said finger sidewall being substantially flat;
a thumb section for contact with the thumb of the user joined to said handle section, said thumb section including a thumb upper wall, a lower wall, a first sidewall and a second sidewall, said thumb section with a distal end and an opposite end joined to said handle section, said thumb section having a front portion with a first length and a back portion with a second length that intersects said front portion to define an angle, said back portion terminating adjacent to said handle section, said second length being greater than one-half of said first length, a majority of said front portion having a width that is greater than a majority of the widths of each of said outer surface and said inner surface of said handle section; and
a butt surface extending between said outer end of said handle section outer surface and said inner end of said handle section inner surface.

16. A handle, as claimed in claim 15, wherein:
a majority of said front portion is wider than said back portion.

17. A handle, as claimed in claim 15, wherein:
a first angle is defined between a line extending along said butt surface and a line extending along said handle section outer surface, a second angle is defined between a line extending along said butt surface and a line extending from said outer common end of said handle section to said distal end of said thumb section, and a third angle is defined between a line extending along said lower wall of said thumb section and a line extending along said butt surface and in which said line extending along said lower wall does not pass inwardly of said thumb section, said third angle being greater than said second angle and in which said third angle is closer in magnitude to said first angle than to said second angle.

18. A handle, as claimed in claim 15, in combination with:
a working device connected adjacent to one of: (a) said distal end of said thumb section and (b) said butt surface while being closer to parallel to said butt surface than perpendicular thereto.

19. A handle comprising:
a handle section for contact with the palm and fingers of a user including a palm sidewall, a finger sidewall, an outer surface and an inner surface, said outer surface having an outer end and an common outer end, said inner surface having an inner end and a common inner end, said handle section having a cross-section that is substantially ovate, each of said palm sidewall and said finger sidewall being substantially flat;

a thumb section for contact with the thumb of the user joined to said handle section, said thumb section including a thumb upper wall, a lower wall, a first sidewall, and a second sidewall, said thumb section with a distal end and an opposite end joined to said handle section, said thumb section having a front portion with a first length and a back portion with a second length that intersects said front portion to define an angle, said back portion terminating adjacent to said handle section, said second length being greater than one-half of said first length, a majority of said front portion having a width that is greater than the width of said back portion; and a butt surface extending between said outer end of said handle section outer surface and said inner end of said handle section inner surface.

20. A handle, as claimed in claim 19, wherein:

a majority of said front portion is wider than each of said outer and inner surfaces of said handle section.

21. A handle, as claimed in claim 19 wherein:

a first angle is defined between a line extending along said butt surface and a line extending along said handle section outer surface, a second angle is defined between a line extending along said butt surface and a line extending from said common outer end of said handle section to said distal end of said thumb section, and a third angle as defined between a line extending along said lower wall of said thumb section and a line extending along said butt surface, said line extending along said lower wall not passing inwardly of said thumb section, said third angle being greater than said second angle and in which said third angle is closer in magnitude to said first angle than to said second angle.

22. A handle, as claimed in claim 21, wherein:

said first angle is in the range of 65°–85° and said second angle is in the range of 35°–55°.

23. A handle, as claimed in claim 19, in combination with:

a working device connected adjacent to one of: (a) said distal end of said thumb section and (b) said butt surface while being closer to parallel to said butt surface than perpendicular thereto.

* * * * *